United States Patent [19]

Frech et al.

[11] 4,311,680
[45] Jan. 19, 1982

[54] METHOD FOR REMOVAL OF SULFUR COMPOUNDS FROM A GAS STREAM

[75] Inventors: Kenneth J. Frech, Tallmadge; James J. Tazuma, Stow, both of Ohio

[73] Assignee: The Goodyear Tire & Rubber Company, Akron, Ohio

[21] Appl. No.: 208,613

[22] Filed: Nov. 20, 1980

[51] Int. Cl.³ .............................................. B01D 53/34
[52] U.S. Cl. .................................... 423/230; 423/231; 423/234; 423/244; 423/571; 423/573 R; 252/411 S
[58] Field of Search ............... 423/224, 225, 230, 231, 423/244 R, 571, 573 G, 573 R; 252/411 S, 191, 192

[56] References Cited

U.S. PATENT DOCUMENTS

| | | | |
|---|---|---|---|
| 632,400 | 9/1899 | Chollar | 423/224 |
| 1,934,242 | 11/1933 | Smyly | 423/231 |
| 3,969,479 | 7/1976 | Lonnes et al. | 423/224 |

*Primary Examiner*—Earl C. Thomas
*Attorney, Agent, or Firm*—D. O. Nickey

[57] ABSTRACT

This invention relates to a process for the removal of sulfur compounds from a gas stream. More specifically, this invention relates to an improvement in the iron oxide method of sulfur removal from a gas stream through the use of hydrogen peroxide.

11 Claims, No Drawings

METHOD FOR REMOVAL OF SULFUR COMPOUNDS FROM A GAS STREAM

TECHNICAL FIELD

This invention relates to a process for the removal of sulfur compounds such as $H_2S$, mercaptans, sulfides and disulfides from a gas stream. More specifically, this invention describes an improved method for the sweetening of a sour natural gas stream.

BACKGROUND ART

Removal of sulfur compounds from gas streams has been of considerable importance in the past and is even more so today due to environmental considerations. Gas effluent from the combustion of organic materials, such as coal, almost always contain sulfur compounds and sulfur removal processes have been concentrated on removing hydrogen sulfide since it has been considered a significant health hazard and because it is corrosive, particularly when water is present. With increasing emphasis on eliminating or minimizing sulfur discharge to the atmosphere, attention is turning to removal of other sulfur compounds from gas streams.

Sulfur contaminants in natural gas streams include hydrogen sulfide, mercaptans, sulfides, and disulfides which due to their odorous nature can be detected at parts per million (ppm) concentration levels. Thus, it is desirable for residential and commercial users of natural gas to have concentrations of mercaptans lowered to 1 ppm and total concentrations of sulfur compounds to 20 ppm or less.

Numerous natural gas wells produce what is called in the industry as "sour gas." "Sour gas" is natural gas that contains hydrogen sulfide, mercaptans, sulfides and disulfides in concentrations that make its use unacceptable. Considerable effort has been expended to find an effective and cost efficient means to remove these objectionable sulfur compounds from natural gas.

Transmission companies that purchase natural gas from well owners and then distribute to consumers are very critical of sulfur content and require total sulfur content to be less than 30 ppm. Thus, owners of sour gas wells that exceed the 30 ppm limit are constantly searching for new and more efficient means to make their gas salable.

A number of processes are known for the removal of $H_2S$ from natural gas streams. Processes presently available can be categorized as those based on physical absorption, solid absorption or chemical reaction. Physical absorption processes suffer from the fact that they frequently encounter difficulty in reaching the low concentration of hydrogen sulfide required in the sweetened gas stream. Solid bed adsorption processes suffer from the fact that they are generally restricted to low concentrations of $H_2S$ in the entering gas stream. Chemically reacting processes in general are able to meet sweet gas specifications (primarily $H_2S$ concentrations) with little difficulty; however, they suffer from the fact that a material that will react satisfactorily with $H_2S$ will also react with $CO_2$. Above all, the processes presently available do not effectively provide for the removal of mercaptans, sulfides and disulfides.

An example of a chemically reactive process is the ferric oxide fixed bed process, wherein the reactive entity is ferric oxide ($Fe_2O_3$) impregnated on an inert carrier. This process is good for the removal of $H_2S$ but does not appreciably remove mercaptans or other sulfur compounds. The bed can be regenerated; however, the number of regenerations is limited by the buildup of elemental sulfur upon the bed.

The iron oxide or "dry box" process was one of the first developed for removing $H_2S$ from gas streams. It was introduced in England about the middle of the 19th century and is still widely used in many areas in special applications.

The iron sponge method of sulfur removal from natural gas has been widely used during the past quarter century and has been reported in detail in the literature. See, for example, Taylor, D. K. *"High Pressure Dry Box Purification," Proceedings Gas Conditioning Conference, University of Oklahoma*, 1956, page 57; and *The Oil and Gas Journal*, November and December 1956, a series of 4 articles; and Zapffe, F., *"Practical Design Consideration For Gas Purification Processes,"* The Oil and Gas Journal, Sept. 8, 1958, page 100; and Sept. 10, 1962, page 135.

Typically, the iron oxide process apparatus is two towers filled with an inert carrier that is impregnated with iron oxide. Each tower has a means for the injection of water and air so as to allow for regeneration. Ordinarily at least two iron oxide beds will be used in order to provide for continuous operation. "Sour gas" enters the top of the bed and flows downward contacting the iron oxide. Sweetened gas is removed from the bottom of the vessel. The vessel not in operation would normally be shut down for removal or regeneration of the exhausted iron oxide. In the piping and operation of the process, provisions must be made for the introduction of water and maintenance of a slightly basic pH. Water must be added to this process or the gas will gradually dehydrate the ferric oxide, thus causing it to lose its activity.

There are several known forms of ferric oxide. Only the alpha and gamma forms are satisfactory for gas sweetening purposes. The ferric oxide is dispersed on materials or large surface and light weight. The most frequently used material is wood shavings or chips. Dispersing the iron oxide in this way provides a relatively large surface area to weight ratio and maximizes contact between the gas stream and the iron oxide.

The iron oxide process can be operated on a batch basis or continuously, the difference depending upon the technique used for regeneration. When a batch process is used the tower is operated until the bed becomes saturated with sulfur and $H_2S$ begins to appear in the sweetened gas stream. At this point the tower is removed from sweetening service and regenerated by circulating gas containing a small amount of air through the bed. Oxygen concentration of the regeneration stream is normally held below 3 percent because of the highly exothermic nature of the regeneration reaction. In continuous service a small concentration of oxygen may be added to the "sour gas" before entry to the bed. The oxygen in the air reacts with iron sulfide previously formed to regenerate it at the same time ferric oxide is reacting with $H_2S$ in the gas. Each system has advantages and disadvantages and the choice between batch regeneration and continuous regeneration is based on economic factors which differ from installation to installation.

Theoretically, one pound of ferric oxide will react with 0.64 lbs. of hydrogen sulfide. In field operation this level is never reached. Generally, at 80–85% of theory, $H_2S$ will begin to break through and show up in the gas stream. At this point the bed is shut down and regenerated. For continuous regeneration, D. K. Taylor, *The Oil and Gas Journal,* 54, 125 (Nov. 5, 1956); 54, 260 (Nov. 19, 1956); 54, 139 (Dec. 3, 1956); 54, 147 (Dec. 10, 1956); reports that about 2.5 lbs of sulfur may be removed per pound of iron oxide before the oxide must be replaced.

In natural gas service, pressures are normally high and pressure drop through the bed is not a serious factor.

It has been reported that cycle time of an iron sponge unit in the field is usually 30 days. A long cycle time is desired to minimize bed replacement costs. Regardless of the regeneration methods that are employed today the bed will eventually plug with sulfur and have to be replaced. This requires manual labor which is expensive. Taylor in the reference above gives an excellent summary of points to consider in the design of towers for an iron oxide process for ease of bed replacement and operation.

Primarily the iron sponge process has been applied to the removal of hydrogen sulfide. The iron sponge will also remove minute amounts of mercaptans from a natural gas stream but this process is not well characterized nor is it efficient.

The affinity of iron oxide for hydrogen sulfide and mercaptans is quite different. While the iron oxide has a strong persistent affinity for hydrogen sulfide, its capacity for removal of mercaptans in the presence of hydrogen sulfide is much lower. This results in "break out" of mercaptans in the early stages of iron oxide bed life. Thus, in order to maintain the desired level of sulfur compounds in the treated stream it is necessary to periodically regenerate the iron oxide. The data obtained utilizing the process of the present invention indicates that this is very efficiently carried out by periodic or continuous treatment of the iron oxide bed with hydrogen peroxide solution which also provides an unexpected improvement in the iron oxide's ability to remove mercaptans.

The unexpected advantages attained by the present invention are:

1. $Fe_2O_3$ bed has higher capacity for mercaptans.
2. Wide latitude of regeneration treatment (concentration of hydrogen peroxide) allows for fine tuning the regeneration step to the amount and types of sulfur compounds present in the gas stream.
3. A single treater can remove sulfur compounds to desirable limits for commercial and residential uses.
4. Extends the effective life of the iron oxide bed for removal of various sulfur compounds from natural gas and other gas streams.

A process which improves the ability of an iron sponge to remove sulfur compounds from a gas stream is in demand. The process of the present invention accomplishes effective and economical removal of sulfur compounds from a gas stream through use of hydrogen peroxide in combination with a ferric oxide treatment bed. The reaction of ferric oxide with hydrogen sulfide has been well documented, however, the literature and publications do not disclose a method in which hydrogen peroxide is added to the ferric oxide bed so as to enhance the ability of the ferric oxide bed in the removal of $H_2S$ and mercaptans from a gas stream.

It is the novel and nonobvious use of hydrogen peroxide in the process of the present invention to remove sulfur compounds from a gas stream that comprises at least a portion of the present invention.

DISCLOSURE OF INVENTION

There is disclosed a process for removing hydrogen sulfide, sulfides and mercaptans from gas streams which comprises the steps in combination of:

(a) contacting the gas stream with an oxide of a metal selected from the group consisting of iron, chromium, cobalt, lead, manganese, molybdenum, nickel, copper, vanadium, zinc, tungsten and antimony;

(b) introducing an aqueous solution of hydrogen peroxide on the metal oxide while continuing to contact the gas stream with the metal oxide.

The applicants have found that ferric oxide deposited on an inert material such as activated carbon, vermiculite and wood chips is the most economical and commercially available material.

In addition, it is necessary that the ferric oxide have and maintain either the alpha or gamma forms.

There is also disclosed a process for removing $H_2S$, mercaptans, sulfides and disulfides from a gas stream wherein said gas stream is contacted with ferric oxide deposited upon an inert carrier, the improvement comprising continuously or periodically introducing aqueous $H_2O_2$ on the ferric oxide while continuing to contact the gas stream with said ferric oxide.

Other bed materials may be employed. These bed materials are composed of an inert material on which is deposited or impregnated a substance capable of reacting with $H_2S$. Examples of such materials are oxides of Cr, Co, Pb, Mn, Mo, Ni, Cu, V, Zn, W and Sb.

The applicants have found that the use of a caustic solution in the process of the present invention is not necessary, but useful in solubilizing and reaction products from the reoxidation of the treatment bed. Aqueous solutions of NaOH, KOH, $Na_2CO_3$, $CaCO_3$ and $Ca(OH)_2$ have been found to be appropriate.

Use of the ferric oxide system as taught in the literature is dependent on hydrate formation for maximum activity and is susceptible to difficulties in regeneration. Presently commercial "state of the art" methods exist whereby iron sponge bed can be regenerated. This is accomplished in two ways: (1) constant onstream regeneration by introduction of air (oxygen) through a compressor blower to obtain an oxygen level based on the gas flow of up to 2 percent; and (2) offstream regeneration of the bed by introduction of air by compressor blower over a period of 8 hours or until virtually all the iron sulfides have been converted to oxides. Both methods are costly as they require high power consumption and have high capital requirements. In addition, both methods do not provide water to maintain the optimum state of hydration and the offstream addition of regeneration air interrupts production.

The present invention (1) allows the iron oxide to maintain a high state of reactivity in an onstream manner; (2) increases bed life; (3) reduces the chemical requirements in a secondary treater, if used; (4) accomplishes sulfur removal from the gas stream without resorting to costly compressor blower systems which require high power/labor requirements; and (5) provides simultaneously a means of maintaining the iron sponge bed at optimum level of hydration.

The process of the present invention can be employed with or without the use of a secondary treater. By secondary treater is meant a treatment process which further eliminates or reduces the amount of sulfides and disulfides in the gas stream, subsequent to treatment by the process of this invention. Examples of said secondary treatments can be found in applicants' patent application, serial no. 130,897 filed Mar. 17, 1980, entitled, "Method for Removal of Sulfur Compounds From a Gas." Said application is herein made a cross-reference to this present application.

The temperature of the treatment system is maintained at a temperature of at least 0° C. to prevent water vapor from freezing, however, a more preferred temperature range is from 5° to 80° C. with the most preferred range being from 5° to 35° C.

The gas flow rate and the volume of the treater is such that the retention time in the treater is sufficient to remove a major portion of the $H_2S$, mercaptans, sulfides and disulfides from the gas stream.

Those skilled in the art will readily be able to determine the values of the variables in the treatment so as to substantially reduce sulfur content in the gas stream.

A caustic solution such as aqueous NaOH can be employed in the treatment vessel. Alkalinity is preferred so as to assist the regeneration of the ferric oxide bed.

The use of a secondary treater in the process of this invention is not essential; however, such use may be needed if the sulfur load or composition of the gas stream (sulfur compounds) is such that the primary treater or process of the present invention is unable to remove the necessary amount of sulfur compounds from the gas stream to meet the desired specification.

The process of this invention was tested on a high pressure natural gas stream. There would be minor modifications in the process flow for use of a low pressure gas such as coke oven gas or boiler gas. However, the basic principles of operation would remain the same.

The process of the present invention overcomes the limiting capacity of iron oxide treatment for a variety of sulfur compounds. The process of this invention enhances this capacity by the use of an oxidant such as hydrogen peroxide.

To one skilled in the art the amount and concentration of $H_2O_2$ sprayed onto the treatment bed can be easily determined. Enough aqueous $H_2O_2$ should be used so as to lower the sulfur content of the gas stream to a predetermined level. Excess usage of $H_2O_2$ can be prevented by use of stoichiometric calculations based on input gas analysis.

Low concentrations of $H_2O_2$ (i.e. less than 25%) can be used in the process of this invention, however, several problems can be encountered:

(1) excessive water flow through the bed will cause the $Fe_2O_3$ coating on the bed to be washed off causing pipe plugging problems;

(2) where sub 0° C. temperatures are encountered low concentrations of $H_2O_2$ freeze (i.e. 20 percent freezes at $-7°$ C.);

(3) increased cost of transporting $H_2O$ to and from the treatment site.

High concentrations of aqueous $H_2O_2$ (i.e. greater than 90%) are suitable for use in the process of this invention, however, extreme caution must be exercised in the field when such high concentrations of $H_2O_2$ are used. In addition, the freezing point of 90% aqueous $H_2O_2$ is only $-12°$ C. and will therefore limit the application.

The applicants have discovered that pumping amounts of at least 25% $H_2O_2$ on the iron sponge treatment bed will not only provide for the reactivation of the iron sponge but also assist in the removal of sulfur compounds such as mercaptans, sulfides and disulfides.

Additionally, use of $H_2O_2$ unexpectedly provides residual capability for removing sulfur compounds long after $H_2O_2$ addition is stopped.

Use of $H_2O_2$ in concentrations less than 25% are possible, but applicants have found that concentrations of less than 25% become economically inefficient.

As discussed earlier the reaction of hydrogen sulfide with ferric oxide is well-known; however, all the references and other literature would lead one skilled in the art to believe that use of an oxidant such as $H_2O_2$ would not be possible due to the thermodynamic and kinetic limitations of the reaction of $H_2O_2$ with ferric sulfide and directly with $H_2S$ and/or mercaptans. The literature discloses air oxidation of the ferrous sulfide bed back to ferrous oxide with long reaction times and equilibriums far short of complete rejuvenation.

One may make the argument that use of $H_2O_2$ in place of oxygen or air for the rejuvenation of the ferric oxide bed would be obvious, since two molecule of $H_2O_2$ degrade to 2 molecules of $H_2O$ and one of $O_2$. Thus, one skilled in the art would expect $H_2O_2$ to provide the same results that air or $O_2$ injection would provide. The applicants have discovered, however, that use of $H_2O_2$ to regenerate the ferric oxide bed provides an unexpected result in that removal of $H_2S$ and mercaptans, by the iron sponge bed is enhanced and prolonged, in effect when compared to $O_2$ injection. Example III which follows will demonstrate this unexpected result.

The use of $H_2O_2$ in the process of this invention provides for periodic or continuous regeneration of the iron oxide bed which in turn provides for effective removal of sulfur compounds from a gas stream.

BEST MODE FOR CARRYING OUT THE INVENTION

The following examples are intended to illustrate and not to limit the scope of the present invention.

Analysis of the gas stream in the following examples was conducted prior to and subsequent to treatment by the process of this invention. Gas samples were analyzed by a Barton Recording Sulfur Analyzer Model 286 by means of a slip stream. The Barton 286 Analyzer has a sensitivity of 0.02 ppm of $H_2S$ by volume, 0.02 ppm mercaptans by volume, 0.04 ppm organic sulfides by volume and 0.04 ppm sulfur dioxide with an accuracy of plus or minus 2%. Percent by volume readings were converted to percent by weight and recorded. (ppm equals parts per million).

It should be noted that the following experiments were conducted on a commercial scale so as to illustrate the ability of the process of the present invention to fulfill a long felt commercial need.

EXAMPLE 1

Ferric Oxide and $H_2O_2$ Treatment To Remove Sulfur Compounds from a Natural Gas Stream The treatment vessel used in this experiment is a 1.22 meter by 3.05 meter vertical cylindrical vessel with an approximate volume of 3.56 cubic meters. The treatment vessel was charged with 3.11 cubic meters of redwood chips coated with ferric oxide.

The redwood chips coated with ferric oxide were "IC" Shavings manufactured and sold by Connolly-GPM, Inc. of Chicago, Ill., which contains 193.2 kilograms of $Fe_2O_3$ per cubic meter. A portion of the ferric oxide chips were added to the vessel. Water was added to give 5–10% by wt. content and then the chips compacted by tamping. The process of chip addition, wetting with water and compaction continued until the vessel was filled. The vessel was then closed and made pressure tight. At this point the treatment vessel was ready for service.

The gas subjected to treatment was taken from a wellhead which produces approximately 1000 lb/sq. in. pressure. It contains an average of 200 ppm's sulfur compounds by weight. A typical wellhead sample relative to sulfur containing compounds was found to be:

TABLE I

| S-Compound | ppm by wt. |
|---|---|
| $H_2S$ | 142 |
| $CH_3SH$ | 2 |
| $C_2H_5SH$ | 18 |
| $C_3H_7SH$ | 17 |
| $C_4H_9SH$ | 4–5 |
| Alkyl sulfides | 11–12 |
| $C_5H_{11}SH$ | 4–5 |
| Others | 1–2 |
| Total | 199–203 |

Prior to treatment the gas was separated from any liquid or solid phase material.

The operating conditions are set out as follows:

| Gas Flow | 875–925 mcf per day* |
|---|---|
| Vessel Pressure | 200–215 psi |
| Treatment Temperature | 45–70° F. (7–22° C.) |
| Concentration of $H_2O_2$/ by wt. | 50% |

*(mcf = thousand cubic feet)

The flow rate and pressure were established as set out above. The ability of the $Fe_2O_3$ bed to remove sulfur compounds was monitored for 4 weeks. Initially the $Fe_2O_3$ bed was able to satisfactorily remove $H_2S$ and partially remove mercaptans, however, after 4 weeks $H_2S$ and appreciable amounts of mercaptans began to breakthrough. The Table below sets out the gas composition before treatment, the gas composition after treatment initially and gas composition after 4 weeks.

TABLE II

| | Gas Concentration:ppm by wt. | | |
|---|---|---|---|
| Component | Untreated | Outlet $Fe_2O_3$ Treat. Start | Outlet $Fe_2O_3$ Treat. Plus 4 Wks. |
| $H_2S$ | 142 | 0 | 10–20 |
| Mercaptan | 43–45 | 17–20 | 43–45 |
| Sulfides | 11–12 | 11–12 | 11–12 |
| Residual S Compounds | 4–7 | 4–7 | 4–7 |
| Total | 202–208 | 32–39 | 68–84 |

After four weeks on line it is evident that the $Fe_2O_3$ bed is unable to reduce the sulfur compounds to acceptable levels. At this point the $Fe_2O_3$ bed is considered spent. To illustrate the ability of $H_2O_2$ to regenerate the activity of the $Fe_2O_3$ bed while still on line, pumping of 50% $H_2O_2$ by wt. was begun at the rate of 1.5 gallons/hour. Immediately upon pumping $H_2O_2$ the on-line sulfur analyzer registered a decrease. The following table illustrates this effect.

TABLE III

| | $H_2O_2$ Addition on Spent $Fe_2O_3$ Bed | |
|---|---|---|
| | Gas Composition - ppm by wt. | |
| Time (min.) | Outlet of Treater S content ppm | Quantity of 50% $H_2O_2$ Pumped-Gallons (total) |
| 0 | 76 | 0 |
| 30 | 57 | 0.8 |
| 60 | 46 | 1.6 |
| 90 | 42 | 2.4 |

After 90 minutes of pumping 50% $H_2O_2$ (2.4 gallons) the pump was shut down and gas continued to flow through the $Fe_2O_3$ bed overnight. The following Table illustrates how periodic addition of $H_2O_2$ can maintain the needed activity of the $Fe_2O_3$ bed.

TABLE IV

| Time between $H_2O_2$ Addition (Hours) | S-ppm by wt. Outlet of $Fe_2O_3$ Treater | Duration of $H_2O_2$ Pump. (min.) | Gallons 50% $H_2O_2$ Pumped |
|---|---|---|---|
| 19.5 | 54 | — | — |
| Added $H_2O_2$ | 21 | 90 | 2.2 |
| 15.5 | 31 | — | — |
| Added $H_2O_2$ | 20 | 150 | 4.0 |
| 13.0 | 25 | — | — |
| Added $H_2O_2$ | 21 | 255 | 6.8 |
| 16.5 | 25 | — | — |
| Added $H_2O_2$ | 23 | 240 | 6.4 |
| 15.5 | 27 | — | — |
| Added $H_2O_2$ | 20 | 60 | 1.6 |
| 14.5 | 30 | — | — |

Table IV illustrates the ability of hydrogen peroxide to maintain the ability of the iron sponge to substantially remove $H_2S$ from the gas stream while also aiding in the removal of mercaptans.

EXAMPLE 2

The procedure of Example 1 concerning the preparation of the treatment bed was followed except that $H_2O_2$ was pumped from the beginning so as to compare the process of the present invention with what is presently used in the field.

The Table V following contains data collected over a period of 36 days.

TABLE V

| Time Days After Start | Outlet $Fe_2O_3$ Treater-Total S Content-ppm by wt. | 50% $H_2O_2$ Aqueous Sol. Pumped:Gal Cumulative | Gas Flow Ratio Rate MCF Cumulative |
|---|---|---|---|
| 1 | 15 | 3.6 | 320 |
| 3 | 16 | 15.8 | 1970 |
| 5 | 17 | 25.9 | 3620 |
| 10 | 20 | 48.2 | 7820 |
| 15 | 21 | 64.8 | 12045 |
| 20 | 20 | 79.2 | 16545 |
| 25 | 20 | 97.9 | 20670 |
| 30 | 16 | 116.6 | 24920 |
| 35 | 16 | 133.6 | 29295 |

After 35 days on line the vessel had treated almost 30,000,000 cubic feet of gas and was still able to satisfactorily reduce Sulfur content from 200 ppm to an average of 17 ppm. To appreciate the effect of this invention one must review the data contained in Table II, where the same $Fe_2O_3$ treater without $H_2O_2$ addition after 28 days allowed 68–84 ppm sulfur containing gas to pass.

The following example is provided to contrast the process of the present invention with what is presently used in the field, $O_2$ injection into the gas stream prior to treatment to rejuvenate the bed. The treatment vessel and gas parameters are set out in Example 1.

EXAMPLE 3

The treatment vessel was prepared as in Example 1 and gas flow initiated. Pumping of 50% $H_2O_2$ by weight was begun shortly thereafter and continued for one hour for a total pumping of $H_2O_2$ of 1.7 gal. which is 8.5 lbs. of $H_2O_2$ or approximately 4 lbs. of active $O_2$ or a volume of 57 ft.$^3$.

TABLE VI

| Time | Outlet Treater S-content ppm | |
|---|---|---|
| 0750 | 33.4 | pumped 1.7 gals. 50% aqueous |
| 0850 | 20.0 | $H_2O_2$ on bed |
| 0190 | 20.9 | |
| 0935 | 22.7 | |
| 1005 | 23.6 | |
| 1040 | 25.5 | |

As indicated from the data $H_2O_2$ addition provides for significant sulfur removal even after $H_2O_2$ has stopped.

The bed continued to have gas pass through it until 1905 hours when $O_2$ addition began. 60 ft.$^3$ of $O_2$ was injected into the gas to be treated before it entered the treatment vessel in a one hour period.

The following table sets out the data collected.

TABLE VII

| Time | Outlet Treater S-Content ppm | |
|---|---|---|
| 1900 | 49.3 | |
| 1905 | 49.3 | 60 ft.$^3$ $O_2$ added |
| 1945 | 26.1 | to gas prior to |
| 2005 | 26.0 | treatment |
| 2015 | 27.3 | |
| 2115 | 39.1 | |

The data from Table VII indicates that once $O_2$ injection ceases sulfur content goes up unlike an equal amount of $H_2O_2$ which provides some reserve capacity.

To make sure that the rate of $O_2$ addition was sufficient a second test was run wherein the 60 ft.$^3$ $O_2$ was injected in 30 minutes. The following Table sets out the data collected.

TABLE VIII

Using the same bed $O_2$ injection began at 2120 hours and stopped at 2150 hours during which 60 ft.$^3$ of $O_2$ was injected into the gas stream prior to treatment.

| Time | S-Content Outlet of Treater | |
|---|---|---|
| 2115 | 39.1 | |
| 2120 | 43.5 | |
| 2140 | 22.1 | 60 ft.$^3$ $O_2$ injected |
| 2150 | 22.7 | |
| 2205 | 24.5 | |
| 2230 | 33.6 | |
| 2245 | 39.7 | |

Table VIII indicates that no matter what rate the $O_2$ is added, once it stopped the sulfur content of the effluent from the treater immediately goes up.

After secondary treatment by the process disclosed in U.S. Patent Application Ser. No. 130,897, filed Mar. 17, 1980, gas samples were taken near the end of each run as set out in Tables VI, VII, and VIII and a sulfur compound component analysis was carried out. The data is presented in Table IX.

TABLE IX

| End of Run Set Out | Total S Content PPM Post Secondary Treat. | Mercaptan % | Sulfides % | Polysulfide & Residual S |
|---|---|---|---|---|
| Table VI | 14.4 | 0.0 | 11.6 | 2.8% |
| Table VII | 17.9 | 2.8 | 11.6 | 3.5 |
| Table VIII | 15.7 | 1.9 | 11.0 | 2.8 |

The effect of the secondary treatment on these results is equal for each test and thus does not influence the comparative analysis. A study of the data contained in Table IX clearly indicates that the process of the present invention is superior to that presently used and provides an unexpected result in that the removal ability of the ferric oxide bed for mercaptans, sulfides and $H_2S$ is enhanced.

This Example amply demonstrates the nonobvious advantages that can be obtained through the use of the process of this invention over the $O_2$ injection methods presently used commercially.

The data just provided illustrates the use of $H_2O_2$ addition to a one-stage treatment process. The process of the present invention is also adaptable to dual or multistage treatment processes wherein the treatment described in this invention, that being the addition of $H_2O_2$ to an iron sponge bed may precede or be subsequent to another treatment process. Also, two or more iron sponge beds may be used in series with $H_2O_2$ being added to each bed in varying amounts.

It would be evident to those skilled in the art that the amount and concentration of the $H_2O_2$ added will depend upon the concentrations of the incoming gas and the restriction requirements on the sulfur content of the effluent.

INDUSTRIAL APPLICABILITY

The process of this invention which employs the use of $H_2O_2$ in conjunction with a ferrous oxide bed has numerous industrial applications. An effective and economical means for removing sulfur compounds, specifically $H_2S$, sulfides, disulfides, and mercaptans from a gas stream has been long needed. Through the use of this invention sulfur compounds can be removed from a gas stream. For example, effluent from coke ovens, sewage plants, paper mills and in particular, sour natural gas streams. Conversely, this invention can be used to remove sulfur compounds from gas streams entering vessels, hospitals, buildings and etc.

While certain representative embodiments and details have been shown for the purpose of illustrating the invention it will be apparent to those skilled in this art that various changes and modifications may be made therein without departing from the spirit or scope of this invention.

We claim:
1. A process for removing hydrogen sulfide, sulfides and mercaptans from a gas stream which comprises the steps in combination of:
   (a) contacting the gas stream with an oxide of a metal selected from the group consisting of iron, chromium, cobalt, lead, manganese, molybdenum, nickel, copper, vanadium, zinc, tungsten and antimony;

(b) introducing an aqueous solution of hydrogen peroxide on the metal oxide while continuing to contact the gas stream with the metal oxide.

2. A process according to claim 1 wherein the gas stream is natural gas and is subsequently treated until a desired level of H$_2$S, mercaptans and sulfides is obtained.

3. A process according to claim 1 wherein the concentration of aqueous H$_2$O$_2$ is at least 25% by weight.

4. A process according to claim 1 wherein an aqueous solution of a compound selected from the group NaOH, KOH, Na$_2$CO$_3$, CaCO$_3$ and Ca(OH)$_2$ is introduced upon the metal oxide deposited upon an inert carrier.

5. A process according to claim 1 wherein the form of the ferric oxide is either alpha or gamma or both.

6. A process for removing H$_2$S, sulfides and mercaptans from a gas stream wherein said gas stream is contacted with ferric oxide deposited upon an inert carrier, the improvement comprising continuously or periodically introducing aqueous H$_2$O$_2$ on the ferric oxide while continuing to contact the gas stream with said ferric oxide.

7. A process according to claim 6 wherein the gas stream is natural gas and is subsequently treated until a desired level of H$_2$S, mercaptans and sulfides is obtained.

8. A process according to claim 6 wherein the concentration of aqueous H$_2$O$_2$ is at least 25% by weight.

9. A process according to claim 6 wherein an aqueous solution of a compound selected from the group NaOH, KOH, Na$_2$CO$_3$, CaCO$_3$ and Ca(OH)$_2$ is introduced upon the metal oxide deposited upon an inert carrier.

10. A process according to claim 6 wherein the form of the ferric oxide is either alpha or gamma or both.

11. A process according to claim 1 or 6 wherein the gas stream is natural gas and the metal oxide is ferric oxide.

* * * * *